United States Patent [19]

Panzone et al.

[11] Patent Number: 5,378,837
[45] Date of Patent: Jan. 3, 1995

[54] PROCESS FOR PREPARING 2'-(DIETHYLAMINO)RIFAMYCIN P (P/DEA)

[75] Inventors: Gianbattista Panzone, Cornaredo; Anacleto Gianantonio, Milan, both of Italy

[73] Assignee: Gruppo Lepetit S.p.A., Gerenzano, Italy

[21] Appl. No.: 134,515

[22] Filed: Oct. 8, 1993

Related U.S. Application Data

[63] Continuation of Ser. No. 975,223, Nov. 12, 1992, abandoned, which is a continuation of Ser. No. 823,237, Jan. 21, 1992, abandoned.

[30] Foreign Application Priority Data

Jan. 28, 1991 [EP] European Pat. Off. ........... 91101037

[51] Int. Cl.$^6$ .................... A61K 31/395; C07D 513/18
[52] U.S. Cl. .................... 540/456; 540/457; 540/458
[58] Field of Search .................... 540/456, 457, 458

[56] References Cited

U.S. PATENT DOCUMENTS

| | | | |
|---|---|---|---|
| 4,116,957 | 9/1978 | Rossetti et al. | 540/457 |
| 4,129,562 | 12/1978 | Cricchio | 540/457 |
| 4,144,234 | 3/1979 | Cricchio | 540/457 |

FOREIGN PATENT DOCUMENTS

| | | | |
|---|---|---|---|
| 872294 | 3/1979 | Belgium | 540/456 |
| 0228606 | 12/1986 | European Pat. Off. | 540/457 |
| 2548128 | 10/1975 | Germany | 540/456 |
| 1470426 | 8/1974 | United Kingdom | 540/457 |

OTHER PUBLICATIONS

Journal of Medicinal Chemistry, vol. 33, No. 5, (1990), *Synthesis and Biological Activity of Some Derivatives of Rifamycin P,* Cavalleri, et al., Washington US pp. 1470–1476.

Journal of American Chemical Society; 98:22; Oct. 27, (1976); *Substituent Effects on the Solution Conformation of Rifamycin S;* M. F. Dampier, et al., pp. 7064–7069.

Bactericidal Activity in Vito of Various Rifamycins against Mycobacterium avium and Mycobacterium tuberculosis; Heifets, et al.

*Primary Examiner*—Robert T. Bond
*Attorney, Agent, or Firm*—J. Michael Dixon

[57] ABSTRACT

The present invention relates to a new one-pot process for preparing 2'-(diethylamino)rifamycin P and its 25-desacetyl derivative which consists in cyclizing 3-bromorifamycin S or its 25-desacetyl derivative, dissolved in dimethylformamide, with 1,1-diethylthiourea and reducing, without isolation, the obtained 1,2-quinonimine intermediate with a mild reducing agent.

12 Claims, No Drawings

PROCESS FOR PREPARING 2'-(DIETHYLAMINO)RIFAMYCIN P (P/DEA)

This is a continuation of application Ser. No. 07/975,223, filed Nov. 12, 1992, now abandoned, which is a continuation of application Ser. No. 07/823,237, filed Jan. 21, 1992, now abandoned.

The present invention concerns a new one-pot process for preparing 2'-(diethylamino)rifamycin P (P/DEA) and its 25-desacetyl derivative of formula I:

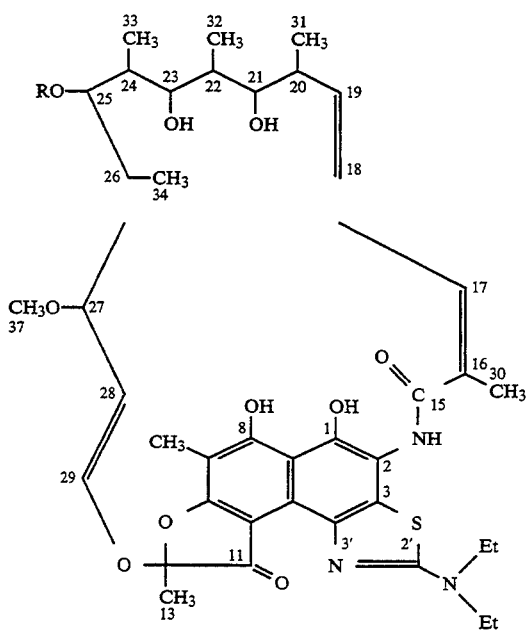

wherein R is acetyl or hydrogen that does not require either isolation of intermediate compounds or chromatographic purifications.

P/DEA is under investigation as potential drug for the treatment of *Mycobacterium avium* complex (MAC) infections because of its high and uniform activity against this type of bacterium together with its low toxicity and good oral absorption (see B. Cavalleri et al., J. Med. Chem., vol.33, pp 1470–1476, 1990; L. B. Heifets et al., Am. Rev. Respir. Dis., vol.141, pp 626–630, 1990).

*Mycobacterium avium* complex (MAC), including *M. avium intracellulare* is a common cause of disseminated infections in patients with AIDS and chronic lung infections in immunocompromised patients.

2'-(Diethylamino)rifamycin P or 4-deoxy-2'-(diethylamino)thiazolo[5,4-c]rifamycin SV is a synthetic derivative of rifamycin P, a thiazole rifamycin wherein a thiazole ring is condensed on positions 3 and 4 of the rifamycin molecule.

4-Deoxythiazolo[5,4-c]rifamycin SV (also called rifamycin P) has been obtained both by fermentation of *Nocardia* strains and by chemical processes. The fermentation process has been disclosed in British patent N.1470426 while chemical processes are reported in U.S. Pat. Nos. 4,144,234 and 4,129,562.

P/DEA is claimed together with its 25-desacetyl derivative and other 2'-(N,N-disubstituted)aminorifamycin P derivatives in European patent application publication N.228606wherein is prepared, with low yield (6.0%), by reacting rifamycin P with diethylamine in ethyl acetate. This reaction is also applied to a series of heterocyclic amines (particularly N-substituted piperazines) to obtain the corresponding 2'-(cyclic amino) derivatives of rifamycin P but the reported yields are always low (6.0–30%). In an alternative approach (B. Cavalleri et al. J. Med. Chem., vol.33, pp 1470–1476, 1990 ) 2'-(N,N-diethylamino)rifamycin P was obtained by treating 3-bromorifamycin S in methanol with N,N-diethylthiourea (DETU), extracting the reaction mixture with ethyl acetate, and purifying, by preparative TLC, the obtained precipitate by addition of petroleum ether (49% yield). 2'-(N,N-Dibutylamino)rifamycin P was also prepared with lower yields (30%). The process, described in Cavalleri's article, corresponds to the method disclosed in U.S. Pat. No. 4,116,957. This patent discloses 2'-(N-monosubstituted) amino rifamycin P derivatives which are prepared from 3-bromorifamycin S by treatment with N-monosubstituted thioureas in a solvent selected from the group comprising methanol, ethanol, tetrahydrofuran and purification of the isolated raw products by chromatography on silica gel column with overall yield around 50%.

In the above mentioned methods the final products are always impure and must be isolated and purified by chromatography. This makes the processes not suitable for industrial production of P/DEA.

The process of the present invention, which is outlined in scheme I wherein R is acetyl or hydrogen, is a two-step, one-pot process which comprises the reaction of 3-bromorifamycin S (II) in dimethylformamide, with 1,1-diethylthiourea (DETU) in the presence of a hydrobromic acid acceptor to give the green intermediate (III) which is then reduced to P/DEA.

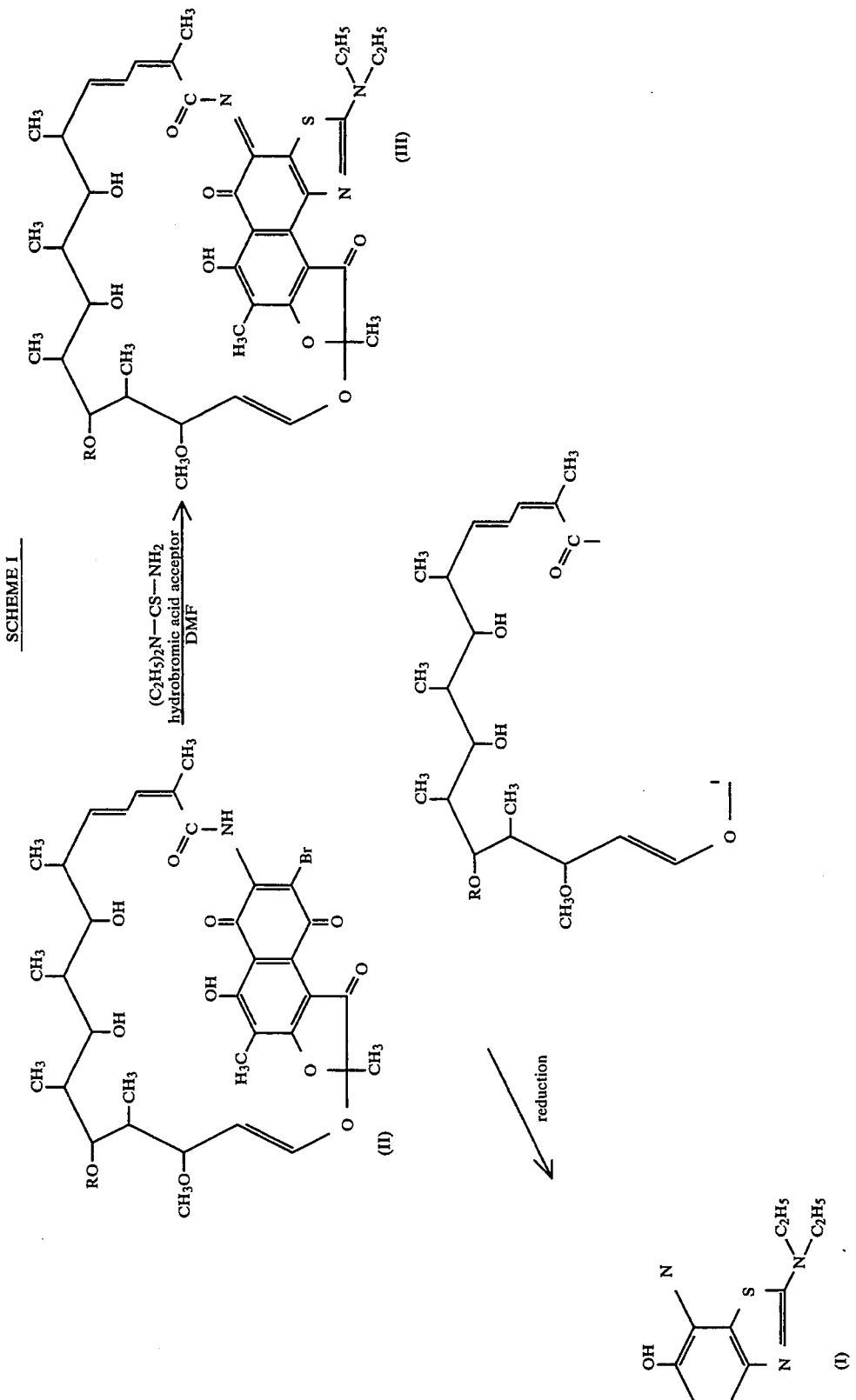
SCHEME I

The intermediate compound (III), which does not require to be isolated, can be easily revealed, as a dark green spot, by thin layer chromatography analysis while its supposed open precursor, on the contrary, cannot be identified in the reaction mixture.

The 1,1-diethylthiourea is preferably employed in a molecular proportion of 1.03 to 1.10 for each mol of 3-bromorifamycin S.

The hydrobromic acid acceptor is preferably selected from tertiary amines, e.g. trialkylamines, pyridine optionally substituted with 1 or 2 ($C_1$–$C_4$)alkyl groups on the carbon moiety, quinoline, N-methylpyrrolidine, N-methylpiperidine, most preferably ($C_1$–$C_4$)trialkylamines, e.g. trimethylamine, methyldiethylamine, triethylamine, methyldibutylamine and it is employed in a molecular amount which is at least equal to that of 3-bromorifamycin S, a moderate (5 to 25%) molar excess over 3-bromorifamycin S being usually preferred.

The reaction temperature may range between 0° C. and 50° C., preferably between 18° C. and 25° C.

The intermediate compound (III) is easily reduced to P/DEA by several mild reducing agents, e.g. sodium bisulfite, sodium metabisulfite or ascorbic acid. In a preferred embodiment of this invention an equivalent amount of reducing agent, i.e. ascorbic acid, was used for each equivalent amount of 3-bromorifamycin S starting material.

P/DEA is then recovered as a crude solid from the reaction mixture, for instance by pouring it into about 8 times its volume of water and filtering.

The pure P/DEA product is finally obtained by crystallization of the dried, crude compound from a suitable solvent, e.g. ethyl acetate.

Analogously, starting from 3-bromo-25-desacetylrifamycin S and following the above process 25-desacetyl-2'-(dethylamino)rifamycin P can be prepared.

The method of this invention does not require any chromatographic purification, the intermediates have not to be isolated because the entire process occurs in the same pot giving the final product in high yield.

In order to find the best conditions of the process many variables were considered by the inventors in explorative trials such as the reaction temperature, the reaction times, and the crystallization solvent.

A preferred range of reaction temperatures is between 18° C. and 25° C. but a wider range of temperatures could be used, with the lower temperatures requiring an increase of the reaction times.

Favorable results were obtained by increasing the reaction time of the final reduction step, e.g. by leaving the reaction mixture containing the intermediate (III) and the reducing agent, e.g. ascorbic acid, at room temperature for one night.

Also the ratio DETU/3-bromorifamycin S was varied. 3-Bromorifamycin S, dissolved in dimethylformamide, was added with a hydrobromic acid acceptor, e.g. triethylamine, and then treated with an excess of 1,1-diethylthiourea (DETU) ransoming from 3–4% to 9–10% without observing a substantial increase in the yields of the final product.

These reaction conditions afford the reaction yields up to about 80% and make the process suitable for industrial production of P/DEA.

To perform the reduction step the reducing agent, e.g. ascorbic acid, is usually added to the dimethylformamide reaction solution containing the intermediate compound of formula (III) in about the same equivalent amount of the starting 3-bromorifamycin S. The reducing agent is preferably dissolved in a mixture of dimethylformamide and water.

Among the solvents considered by the inventors for the final crystallization, ethyl acetate was preferred.

The starting material 3-bromorifamycin S can be prepared according to any of the methods described in the literature (see German patent application publication N.2548128; J.A.C.S. vol.98, p.7064; Belgian patent N.872294).

Analogously, starting from 3-bromo-25-desacetylrifamycin S (see German patent application publication N.2548128) and following the method set forth above, 25-desacetyl-2'-(diethylamino)rifamycin P can be prepared.

25-desacetyl-2'-(diethylamino)rifamycin P can also be prepared in high yield from P/DEA, obtained according to the process of this invention, by treating an ethanol solution of P/DEA with 10% aqueous sodium hydroxide at room temperature under a nitrogen atmosphere. After hydrolysis the reaction mixture is poured into water with stirring and the pH of the resulting solution is brought to 7 with 20% aqueous HCl. The crude solid product is recovered by filtration, dried, and purified by crystallization with ethanol.

EXPERIMENTAL PART

All the HPLC analyses were made with a Hewlett Packard mod.1082 B apparatus equipped with a U.V. (254 nm) detector and a C. Erba RP 18 5 micron 150×4.6 mm prepacked column.

The mobile phases were:
A) 0.025M aqueous $NaH_2PO_4$/$CH_3CN$ 95:5 (v/v)
b) 0.025M aqueous $NaH_2PO_4$/$CH_3CN$ 25:75 (v/v)

All the chromatograms reported were obtained by a linear gradient elation from 50% of (B) in (A) to 85% of (B) in (A) in 35 minutes at a flow rate of 1.3 ml/min.

The TLC separations were obtained using silica gel 60 F254 precoated plates from Merck and a $CH_2Cl_2$/$CH_3OH$ 9:1 mixture as the mobile phase.

The $^1$H-NMR spectra were obtained with a Brucker model AM-500 and were recorded in $CDCl_3$ solution using TMS as internal standard.

LC-MS analysis was carried out on a Hewlett Packard 5985B mass spectrometry interfaced with a HP1090L HPLC via a split-flow DLI probe (also made by Hewlett Packard). Standard conditions were: source temperature 250° C., source pressure $2 \times 10^{-4}$ torr., reverse phase HPLC column (e.g. HPODS 10 cm×4.5 mm, 5 μm packing), eluent $CH_3CN$/$H_2O$ (7:3 v/v). Flow 0.5 ml/min.

The following examples are merely illustrative without limiting the scope of the present invention.

EXAMPLE 1

2,098 g of 3-bromorifamycin S (2.85 mols) were dissolved under stirring in 4.6 l of dimethylformamide (DMF, RPE C.Erba) at 20° C. and 463 ml (3.3 mols) of triethylamine (TEA, RPE C.Erba) were added. After 15 minutes a solution, prepared dissolving 416 g of 1,1-diethylthiourea (DETU, 96% Aldrich, 3.02 mols) in 2.3 l of dimethylformamide, was dripped into in 10 minutes. The ratio DETU mols/3-bromorifamycin S mols was 1.06. The formation of the intermediate compound of formula (III) was monitored each hour by TLC and HPLC.

After 3 hours 501 g of ascorbic acid (98% Aldrich), dissolved in a mixture of 480 ml of water and 870 ml of DMF, were added in order to reduce the intermediate compound of formula (III) to P/DEA. The final reaction mixture was left at room temperature without stirring for one night (15 hours) and, during this time, a plentiful yellow precipitate of P/DEA was obtained. Then it was poured, under stirring, in 55 l of distilled water and the separated solid was recovered by filtration, washed with about 15 l of distilled water to completely eliminate the residual DETU (the solubility of which in water at room temperature is about 1.5 g/l) and dried under vacuum at room temperature for 15 hours.

2740 g of crude P/DEA were obtained. Its HPLC assay was 65% (yield 77%).

The mother liquors, formed by 15% of dimethylformamide and 85% of water, still contained 0.8 g/l of product P/DEA (on the whole 40 g).

Different batches of crude P/DEA of the same purity (HPLC 65%) were blended together (in all 10.97 Kg) and suspended in 70 l of ethyl acetate and the suspension was gently warmed to 50°–60° C. until a complete solution was obtained.

Most of the solvent was then removed (to about ¼ of the initial volume) by distillation under vacuum at 50° C. After cooling to 10°–15° C. the solid was filtered, washed on the filter with 3 l of cold ethyl acetate and dried at room temperature and 20 mm Hg for 48 hours giving 7.140 Kg of pure P/DEA.

Its HPLC assay was 96–97%, the water content (K.F.) 1.4% and the residual solvent 1.3%. The overall yield was 75%.

The mother liquors (23 l) still contained 8.7 g/l of product (in all 200 g, that is 2.8%).

The intermediate compound of formula (III) wherein R is acetyl is quite stable in dimethylformamide solution and in a laboratory trial a small amount of it was also isolated, purified on a chromatographic column and characterized by $^1$H-NMR (Table I) and mass spectrometry (M+2=809, due to the reduction that occurs in the source) suggesting the rifamycin 1,2-quinonimine structure (III).

TABLE I $^1$H-NMR Data (in CDCl$_3$; TMS internal standard, δ 0.00 ppm)
($^1$H, δ ppm)
The spectrum shows the typical NMR pattern of rifamycin S. The attributions are tentatively as follow:

0.158(d, 34-CH$_3$), 0.483(d, 33-CH$_3$), 0.956(d, 31-CH$_3$), 1.01(d, 32-CH$_3$), 1.27(m, 26-H), 1.35(m, two CH$_3$—CH$_2$), 1.41(m, 24-H), 1.66(d, 22-H), 1.71(s, 13-CH$_3$), 2.08(s, 36-CH$_3$), 2.21(s, 30-CH$_3$), 2.22(s, 14-CH$_3$), 2.33(m, 20-H), 3.01(dd, 23-H), 3.1(s, 37-CH$_3$), 3.18(d, 21-H), 3.55(d, 27-H), 3.7(m, two CH$_3$—CH$_2$), 4.8(d, 25-H), 5.25(dd, 28-H), 6.21(d, 29-H), 6.4(dd, 19-H), 6.57(d, 17-H), 6.65(dd, 18-H)

The structure of the intermediate compound (III) was also confirmed by laboratory trials.

In fact P/DEA was rapidly and completely oxidized with N-bromosuccinimide in DMF at room temperature giving on TLC a dark green, less polar spot that was isolated and characterized by $^1$H-NMR and IR confirming the 1,2-quinonimine structure (III).

Even the air can transform P/DEA into this oxidized derivative.

In another laboratory trial a sample of P/DEA was applied to a silica gel thin layer plate and left, without developing, in the air under the hood for 60 hours. After that time a complete transformation of the starting yellow spot, into a green one, was observed. After development with the usual solvent mixture, two dark green spots were found on the plate. The upper one corresponded to the 1,2-quinonimine intermediate of formula (III).

EXAMPLE 2

30 g of pure P/DEA, prepared according to the process of this invention, were dissolved in 300 ml of 95% ethyl alcohol in a 1 l four necked round bottomed flask equipped with a thermometer, a mechanical stirrer and a condenser.

After complete elimination of the oxygen and formation of an inert atmosphere with nitrogen, 80 ml of aqueous 10% sodium hydroxide were added with stirring.

Stirring was continued for another 4 hours at room temperature and the hydrolysis was monitored hourly by TLC analysis.

After this time the reaction mixture was poured, with stirring, into 2 l of distilled water and the pH was brought to 6.9 with aqueous 20% hydrochloric acid. The yellow solid which precipitated was filtered and washed on the filter with about 50 ml of distilled water.

After drying at room temperature for 15 hours, 25 g of crude product were obtained (yield 87.1%).

The mother liquors contained less than 1 g/l of product.

25 g of the crude product were suspended in 600 ml of 95% ethyl alcohol and gently warmed to 60° C. The solution was filtered and then concentrated on a rotary evaporator to 350 ml residual volume. After cooling at 5° C., the solid which separated was filtered, washed on the filter with 50 ml of the same solvent and dried under vacuum at 40° C. for 15 hours.

14.5 g of 96% pure orange-red solid, mp. 214°–216° C., were obtained (64.5% yield).

After a further concentration the mother liquors gave a second crop of 5 g of 94% pure product (total yield 86.1%). The overall yield was 75.6 %.

We claim:

1. A process for preparing 2'-(diethylamino)rifamycin P (P/DEA) or its 25-desacetyl derivative of formula I wherein R is acetyl or hydrogen:

-continued

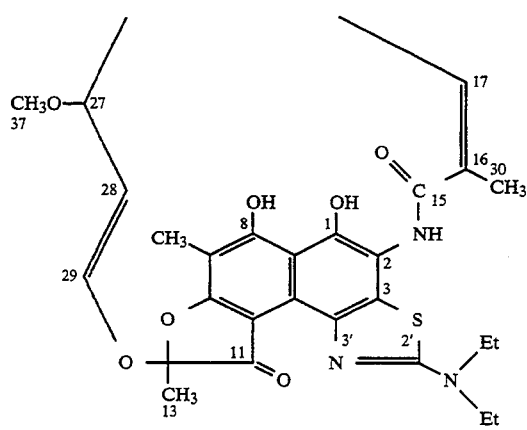

which is characterized in that 3-bromorifamycin S is reacted with 1,1-diethylthiourea in dimethylformamide, in the presence of a hydrobromic acid acceptor, to give a green colored 1,2-quinonimine intermediate of formula III, wherein R has the same meanings as above:

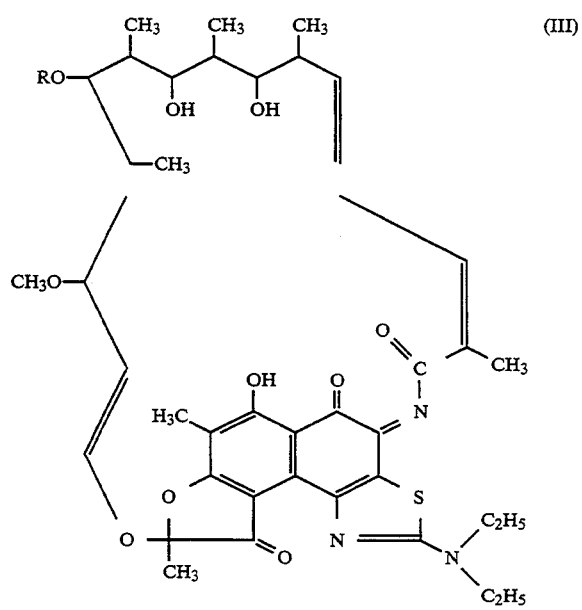

(III)

that is reduced, without isolation, by a mild reducing agent.

2. A process according to claim 1 wherein the 1,1-diethylthiourea is preferably employed in a molecular proportion of 1.03 to 1.10 for each mol of 3-bromorifamycin S.

3. A process according to claim 2 wherein the hydrobromic acid acceptor is preferably selected from tertiary amines, preferably trialkylamines, pyridine optionally substituted with 1 or 2 ($C_1$–$C_4$)alkyl groups on the carbon moiety, quinoline, N-methylpyrrolidine, N-methylpiperidine, most preferably ($C_1$–$C_4$)trialkylamines e.g. trimethylamine, methyldiethylamine, triethylamine, methyldibutylamine.

4. A process according to claim 3 wherein the reaction temperature may range between 0° C. and 50° C., preferably between 18 ° C. and 25° C.

5. A process according to claim 4 wherein the mild reducing agent is ascorbic acid, sodium bisulfite or sodium metabisulfite.

6. A process according to claim 5 wherein the mild reducing agent is ascorbic acid.

7. A process according to claim 6 wherein the mild reducing agent, preferably ascorbic acid, is added to the dimethylformamide reaction solution containing the 1,2-quinonimine intermediate (III) in about the same equivalent amount of the starting 3-bromorifamycin S, preferably dissolved in a mixture of dimethylformamide and water.

8. A process according to claim 7 wherein the reduction of the 1,2-quinonimine intermediate (III) is completed by leaving the final reaction mixture, containing (III) and the reducing agent, preferably ascorbic acid, at room temperature for one night.

9. A process according to claim 8 wherein the reaction mixture containing the crude P/DEA is poured into water, recovered by filtration, and crystallized from ethyl acetate.

10. The 1,2-quinonimine intermediate of formula (III) wherein R is acetyl:

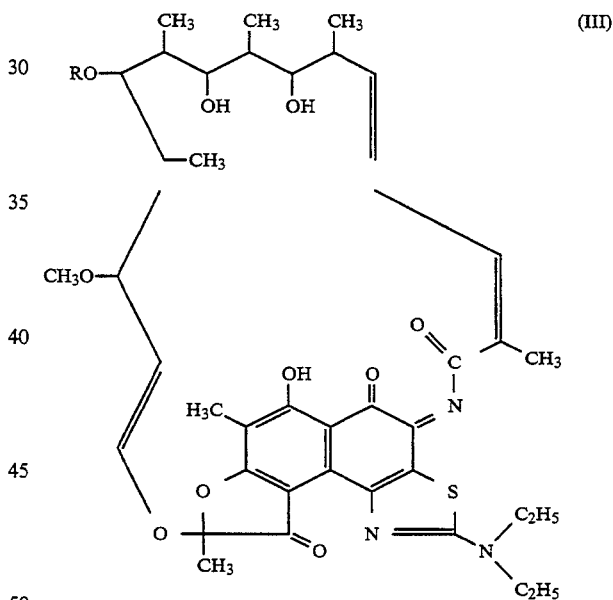

(III)

11. A process for preparing the 1,2-quinonimine intermediate of claim 10 which comprises the reaction of 3-bromorifamycin S in dimethylformamide in the presence of a hydrobromic acid acceptor.

12. A process for preparing 25-desacetyl P/DEA which comprises the hydrolysis of P/DEA, prepared according to the process of this invention, in an alcoholic solvent with a mild alkaline reagent, such as sodium bicarbonate, aqueous sodium hydroxide, organic bases at room temperature under a nitrogen atmosphere.

* * * * *